United States Patent
Tsunazawa et al.

(10) Patent No.: US 8,313,628 B2
(45) Date of Patent: Nov. 20, 2012

(54) METHOD AND APPARATUS FOR EVALUATING DIELECTROPHORETIC INTENSITY OF MICROPARTICLE

(75) Inventors: Yoshio Tsunazawa, Kyoto (JP); Yukihisa Wada, Kyoto (JP); Naoji Moriya, Kyoto (JP); Kenji Takubo, Kyoto (JP); Shinichiro Totoki, Kyoto (JP); Haruo Shimaoka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 770 days.

(21) Appl. No.: 12/374,048

(22) PCT Filed: Jul. 19, 2006

(86) PCT No.: PCT/JP2006/314221
§ 371 (c)(1),
(2), (4) Date: Jan. 15, 2009

(87) PCT Pub. No.: WO2008/010267
PCT Pub. Date: Jan. 24, 2008

(65) Prior Publication Data
US 2010/0012496 A1  Jan. 21, 2010

(51) Int. Cl.
*B03C 5/02* (2006.01)
(52) U.S. Cl. .......................... 204/547; 204/643
(58) Field of Classification Search ................ 204/547, 204/643, 450–470, 600–621
See application file for complete search history.

(56) References Cited

U.S. PATENT DOCUMENTS 5,993,630 A * 11/1999 Becker et al. ................. 204/547
7,760,356 B2   7/2010 Moriya et al.

FOREIGN PATENT DOCUMENTS

| JP | 2006-64659 A | 3/2006 |
| JP | 2006-162332 A | 6/2006 |
| JP | 2006-162333 A | 6/2006 |
| WO | WO-2006/025158 A1 | 3/2006 |

OTHER PUBLICATIONS

International Search Report for the Application No. PCT/JP2006/314221 mailed Oct. 24, 2006.
Yukihisa Wada, "Nanoparticle size analysis with relaxation of induced grating by dielectrophoresis", Optical Express, vol. 14, No. 12, Jun. 12, 2006, pp. 5755-5764.

(Continued)

*Primary Examiner* — Keith Hendricks
*Assistant Examiner* — Kourtney R Carlson
(74) *Attorney, Agent, or Firm* — Cheng Law Group, PLLC

(57) ABSTRACT

A distribution of AC electric field regularly arranged in a cell is formed while storing a sample having particles dispersed in a medium in the cell, whereby the particles are dielectrically migrated in the medium to generate a diffraction grating by density distribution of the particles. Diffracted light generated by irradiating the diffraction grating by density distribution with measuring light is detected, and evaluation of dielectrophoretic intensities of the particles and/or the medium is performed from the detection result. According to this method, evaluation of dielectrophoretic characteristics can be performed without adhering a phosphor to particles, and since even a particle small in size can achieve a detection level by collecting a number of such particles to form a diffraction grating, dielectric characteristics of microparticles of several nanometers in diameter can be thus quantitatively measured with high sensitivity.

6 Claims, 8 Drawing Sheets

OTHER PUBLICATIONS

Yukihisa Wada, "Yuden Eido Grating-ho ni yoru Nano Ryushi Kaiseki", Shimazu Review, vol. 62, Nos. 3 and 4, Mar. 31, 2006, pp. 173-179.
M. Washizu et al., "Molecular dielectrophoresis of biopolymers", IEEE Trans. on Industry Applications, vol. 30, 1994, pp. 835-843.
Nicolas G. Green et al., "Dielectrophoresis of Submicrometer Latex Spheres. 1. Experimental Results", J. Phys. Chem. B, vol. 103, 1999, pp. 41-50.
Masao Washizu et al., "Dielectrophoretic handling of bio-molecules and its application to bio-separation", IEICE (Institute of Electronics, Information and Communication Engineers) Transactions C, vol. J83-C, No. 1, Aug. 2000, pp. 1-8.
Notification of Reasons for Refusal for the Applicaion No. 2008-525748 from Japan Patent Office mailed Feb. 16, 2011.
Yukihisa Wada, "Yuden Eido Grating-ho ni yoru Nano Ryushi Kaiseki" ("DEP Active Grating Method: A New Approach for Size Analysis of Nano-Sized Particles"), Shimazu Review, vol. 62, Nos. 3 and 4, Mar. 31, 2006, pp. 173-179.
Supplementary European Search Report for the Application No. EP 06 78 1228 dated Dec. 7, 2011.

* cited by examiner

US 8,313,628 B2

METHOD AND APPARATUS FOR EVALUATING DIELECTROPHORETIC INTENSITY OF MICROPARTICLE

FIELD OF THE INVENTION

The present invention relates to a dielectrophoretic intensity evaluation method and apparatus for microparticles including so-called nanoparticles of 100 nm or less in particle size.

BACKGROUND OF THE INVENTION

Particles of 100 nm or less in size are generally called nanoparticles, and are just beginning to be used in various fields since they show properties different from those of a general bulk matter composed of the same material. In such a situation, it is becoming important to evaluate the properties of the microparticles.

Dielectrophoresis is known as an evaluation method for microparticle. Dielectrophoresis phenomenon is a phenomenon in which electric polarization is occurred in particles, even if they are charge-free, by applying a strong nonuniform electric field, and the particles are moved due to the attractive force unbalance for polarized positive and negative charges altered by the nonuniform electric field. The intensity of dielectrophoresis is involved by important properties related to physical properties of a particle, such as respective complex dielectric constants of the particle and a medium thereof, and diffusion coefficient. Therefore, by evaluating dielectrophoretic sensitivity of the particle, evaluations for physical properties of the particle and the dispersion medium and for the interaction between the both can be performed.

A typical method for observing the dielectrophoretic intensity of microparticle is direct observation of migrating particles by a microscope. However, the microscopic observation cannot be applied to nanoparticle with a particle size below an optical microscopic observable limit. Therefore, it is proposed to chemically bond a phosphor to the nanoparticle, so that intensity distribution of fluorescent emission can be observed even for a particle smaller than optical resolution. Further, it is known to microscopically observe the process of attracting particles by electrode attractive force and videotape the intensity distribution of fluorescent emission of the particles (refer to, for example, Non-patent Literature 1, 2 or 3), and the dielectrophoretic motion and intensity can be acquired from the video images.

Non-Patent Literature 1: M. Washizu, S. Suzuki, O. Kurosawa, T. Nishizaka, T. Shinohara, "Molecular dielectrophoresis of biopolymers", IEEE Trans. on Industry Applications, vol. 30, 835-843 (1994)

Non-Patent Literature 2: Nicolas G. Green and Hywel Morgan, "Dielectrophoresis of Submicrometer Latex Spheres. 1. Experimental Results", J. Phys. Chem. B, vol. 103, 41-50 (1999)

Non-Patent Literature 3: Masao WASHIZU, Tomohisa KAWABATA, Osamu KUROSAWA, Seiichi SUZUKI "Dielectrophoretic handling of bio-molecules and its application to bio-separation", the IEICE (Institute of Electronics, Information and Communication Engineers) Transactions C, Vol. J83-C, No. 1, pp 1-8, August, 2000

DISCLOSURE OF THE INVENTION

Problems to be Solved by the Invention

The conventional particle evaluation method by dielectrophoresis using video observation of fluorescent particles as described above has the following three disadvantages.

(1) Since the necessity of adhering a phosphor to a target particle is a serious restriction, or the particle cannot be subjected to measurement as it is, this method is not practical for routine analysis, and application thereof is impossible when the phosphor cannot be adhered.

(2) It is difficult to quantitatively determine a migrating force by the video observation.

(3) The most serious difficulty is that this method is not suitable for observation of particles with small particle size such as nanoparticles. The dielectrophoretic force is extremely minimized as the particle size is smaller, since the dielectrophoretic force is proportional to the cube of particle size (or proportional to the volume of microparticle), and the small particle consequently is difficult to be detected. Actually, most of particles treated in the past reports for dielectrophoresis are about µm or about 100 nm in diameter at most, and it would appear that particles of several tens nm or less are difficult to measure.

In view of this circumstance, the present invention provides a dielectrophoretic intensity evaluation method for microparticles, capable of quantitatively evaluating dielectrophoretic force of microparticles including nanoparticles, without performing a pretreatment such as adhesion of a phosphor, and an apparatus for attaining the method.

Means to Solve the Problems

To solve the above-mentioned problems, a dielectrophoretic intensity evaluation method according to the present invention comprises the steps of forming a distribution of AC electric field regularly arranged in a cell while storing a sample having particles dispersed in a medium in the cell, thereby dielectrically migrating the particles in the medium to generate a diffraction grating by density distribution of the particles; detecting diffracted light generated by irradiating the diffraction grating by density distribution with measuring light; and performing characteristic evaluation of the particles and/or the medium from the detection result (first aspect).

In the present invention, frequency dependency of dielectrophoretic intensity or dielectrophoretic sensitivity of a sample can be also evaluated based on a difference in detection result of each diffracted light by performing an operation of forming the distribution of AC electric field in a cell while storing the sample having particles dispersed in a medium within the cell, thereby dielectrically migrating the particles in the medium to generate a diffraction grating by the particles, and detecting diffracted light generated by irradiating the diffraction grating with measuring light, the operation being performed to the same sample more than once by varying frequency of the AC electric field (second aspect).

In the present invention, further, field intensity dependency of dielectrophoretic intensity or dielectrophoretic sensitivity of a sample can be evaluated based on a difference in detection result of each diffracted light by performing an operation of forming the distribution of AC electric field in a cell while storing the sample having particles dispersed in a medium within the cell, thereby dielectrically migrating the particles in the medium to generate a diffraction grating by the particles, and detecting diffracted light generated by irradiating the diffraction grating with measuring light, the operation being performed to the same sample more than once by varying intensity of the AC electric field (third aspect).

In the present invention, further, not only intensity information of the diffracted light generated by irradiating the diffraction grating formed by dielectrophoresis of particles in the medium with the measuring light as described above, but also particle size information of microparticle (the cube thereof is proportional to the volume of the particle) obtained from the temporal attenuation rate of the diffracted light after stopping the AC electric field for dielectrophoresis can be combined for analysis (fourth aspect). As the advantage of this, since the dielectrophoretic intensity depends not only on dielectric constants of the microparticle and the medium but also on the cube of particle size of the microparticle, only dielectric constant information of the microparticle and the medium can be separately extracted by correcting the particle size information based on dielectrophoretic intensity data obtained by acquiring the particle size of the microparticle as described later.

According to the present invention, information for dielectrophoretic intensity in a sample composed of a combination of a medium and particles dispersed therein can be taken out as signal by dielectrically migrating the particles dispersed in the medium within a cell by formation of regular or spatially periodic AC electric field in the cell to generate a diffraction grating by density distribution of the particles, and measuring diffracted light by the diffraction grating, and the intensity of dielectrophoresis can consequently be quantitatively evaluated without needing a pretreatment such as adhesion of a phosphor to the particles.

Namely, when a dielectrophoretic force acts on the particles by forming a regular AC electric field in the sample having the particles movably dispersed in the medium, a density distribution of the particles is caused corresponding to the spatial pattern of the AC electric field as a result of migration of the particles according to the spatial pattern of the electric field, whereby the diffraction grating by density distribution of the particles is generated. Since the intensity of the diffracted light generated by irradiating the diffraction grating with measuring light depends on the magnitude of modulation (contrast) of the diffraction grating by density distribution of the particles, the momentary generation state of diffraction grating can be acquired from the temporal information of the diffracted light. Since the generation rate of diffraction grating is correlated with the dielectrophoretic force of the particles in the medium, the migrating force of the particles in the medium can be evaluated from the manner of increasing of the diffracted light. Further, since particle size information can be obtained from the attenuation rate of the diffracted light after stopping dielectrophoresis through a diffusion coefficient, particle size correction data for dielectrophoretic intensity can be acquired also by the single measurement.

The degree of spatial modulation of the particles can be measured with satisfactory sensitivity only by simply measuring the intensity of the diffracted light of the first order, since the intensity of a specific order (usually, first order) of the diffracted light from the diffraction grating by density distribution is proportional to the square of the periodic spatial modulation degree of the particles.

In general, since the light diffracted from each groove of the diffraction grating is interfered and added in the same phase, signals are increased as the square of the number of grooves, and in the method of the present invention, thus, the sensitivity of measurement can be enhanced by increasing the number of grooves. Therefore, even a particle with small particle diameter can achieve a detection level if a number of such particles collect to form a diffraction grating. It is ascertained that, according to the method of the present invention, dielectrophoretic characteristics can be measured even for microparticles of several nanometers in diameter which are naturally low in dielectrophoretic effect due to the advantages of no need of phosphor, enhanced quantitative determination property, and further improved sensitivity, compared with the conventional evaluation method of dielectrophoresis.

For example, difference in dielectrophoretic force or the like between samples can be quantitatively evaluated by performing the above-mentioned measurement to different samples in the same electric field condition. Difference in dielectrophoretic force or the like to a medium between different kinds of particles can be also quantitatively evaluated by similarly performing the above-mentioned measurement to plural samples, each of them having different kinds of particles dispersed in a common medium in the same electric field condition. Conversely the contribution of different mediums to dielectrophoresis of a kind of particles can be evaluated by performing the above-mentioned measurement to plural samples, each of them having common particles dispersed in a different medium in the same electric field condition.

Further, the frequency dependency of dielectrophoretic intensity or dielectrophoretic sensitivity of a sample can be evaluated from each measurement result by performing the measurement to the same sample with the frequency of the AC electric field being varied as the second aspect of the present invention.

Similarly, the field intensity dependency of dielectrophoretic intensity or dielectrophoretic sensitivity of a sample can be evaluated from each measurement result by performing the measurement to the same sample with the intensity of the AC electric field being varied as the third aspect of the present invention.

Further, particle size information determined from the attenuation rate of diffraction grating after stopping dielectrophoresis can be used, as the fourth aspect of the invention, to correct the term of the cube of particle size contained in the equation of dielectrophoretic intensity.

The dielectrophoretic intensity evaluation apparatus according to the present invention is an apparatus for executing the above-mentioned method of the present invention, which comprises a cell for holding a sample having particles dispersed in a medium; an AC power source; a pair of electrodes for forming an electric field distribution regularly arranged within the cell by applying voltage from the AC power source; a light source for irradiating a diffraction grating resulting from a density distribution caused by dielectrophoresis of the particles by formation of the electric field with measuring light; a light detector for detecting diffracted light of the measuring light by the diffraction grating; and a recording means for recording output of the light detector during the period between starting of voltage application to the electrodes and at least stoppage or modulation of the application.

In the cell of the dielectrophoretic force evaluation device of the present invention, the whole body or at least two wall bodies of the cell through which the measuring light passes are formed of a transparent material such as quartz glass. The electrodes can be adapted to be formed inside the wall bodies composed of the transparent material of the cell, suitably, with a pattern in which a pair of comb-like electrodes each including a plurality of parallel linear electrode pieces connected at one-side end portion is disposed so that each electrode piece of one electrode is fitted to between electrode pieces of the other electrode.

When such comb-like electrodes are arranged, each comb-like electrode is formed so that an electrode piece eccentrically-located area including at least two linear electrode pieces disposed adjacently to each other, and an electrode piece absent area free from electrode pieces are alternately located, and a pattern in which each comb-tooth electrode is disposed so that the electrode piece eccentrically-located area of one comb-like electrode is located in the electrode piece absent area of the other comb-like electrode can be more suitably adopted. By using such electrodes, the pitch of high-density area of particles dielectrically migrated and captured due to formation of the AC electric field by application of AC voltage becomes larger than the pitch of each electrode piece. As a result, the grating pitch of density distribution-induced diffraction grating of the particles becomes larger than the grating pitch of diffraction grating formed by the electrode pieces, and the outgoing directions of diffracted light can be differed between both the diffraction gratings. Thus, the diffracted light by density distribution of the particles can be selectively detected to improve S/N of measurement.

DESCRIPTION OF REFERENCE NUMERAL

Figure 1:
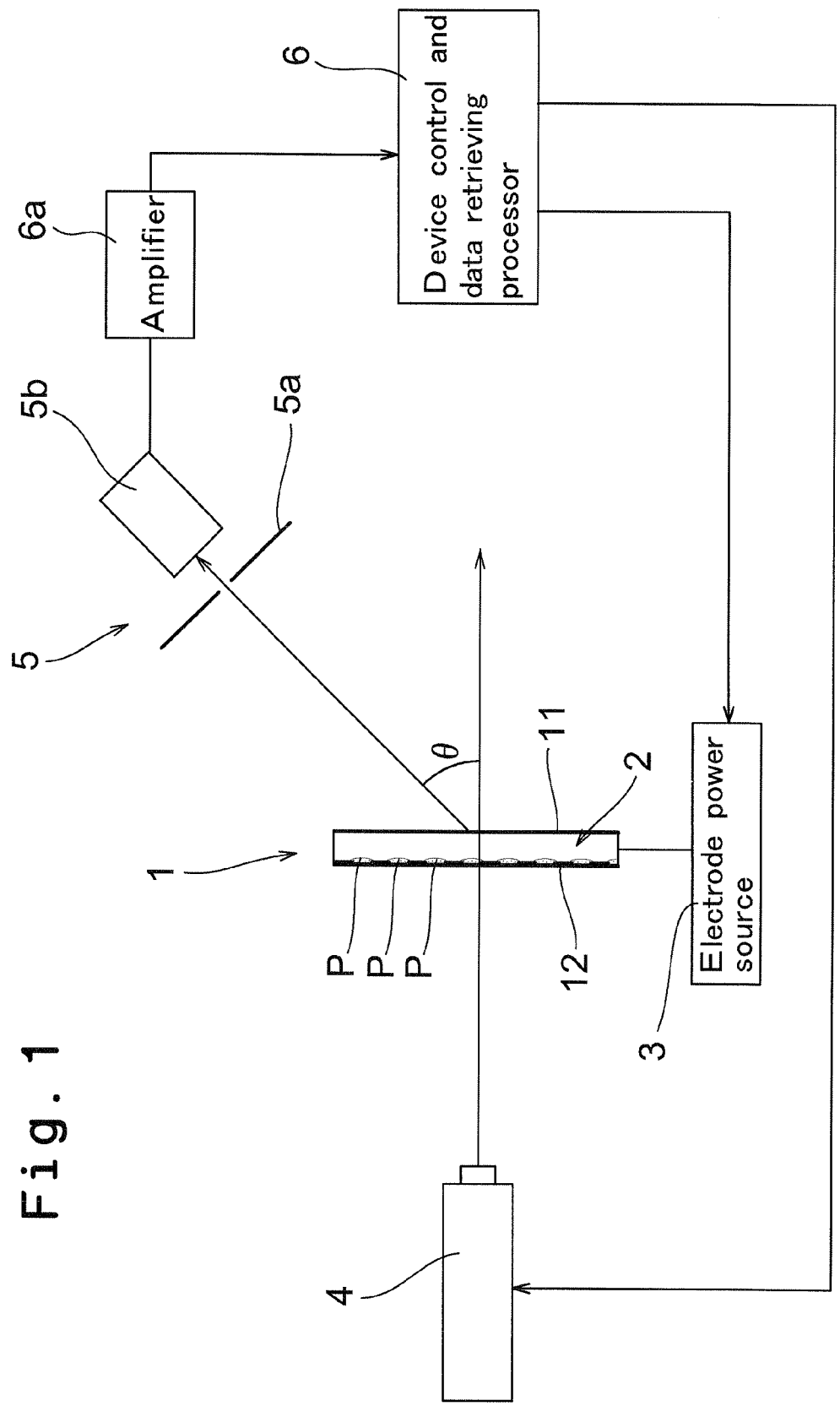
FIG. 1 is a configuration diagram of an embodiment of the present invention, which includes a schematic view showing an optical configuration and a block view showing an electric configuration.

1. Cell
2. Electrode pair
21, 22. Electrode
21a, 22a. Electrode piece
21b, 22b. Connection part
3. Electrode power source
4. Irradiation optical system
5. Detection optical system
6. Device control and data retrieving processor

BEST MODE FOR CARRYING OUT THE INVENTION

Hereinafter, preferred embodiments of the present invention will be described in reference to the accompanying drawings. The present invention is never limited by the embodiments as described below, and various embodiments can be of course included therein without departing from the gist of the present invention. Although the migrating force will be described with view of positive migrating force for capturing particles by attraction, negative migrating force having repelling force also similarly functions as a diffraction grating, with a particle density modulation being formed in the vicinity of the electrodes so that the particle density is lower than in the circumference.

The apparatus, the whole configuration of which is shown in FIG. 1, includes, as main components, a cell 1 for storing a sample having particles movably dispersed therein, for example, a sample having particles dispersed in a liquid, or a sample composed of a gel having particles movably dispersed therein; an electrode power source 3 which applies voltage to an electrode pair 2 provided within the cell 1; an irradiation optical system 4 for irradiating light to the cell 1; a detection optical system 5 for measuring diffracted light from a diffraction grating by density distribution of the particles generated within the cell 1 by the application of voltage to the electrode pair 2; and a device control and data retrieving processor 6 which controls the whole apparatus and also retrieves output from the detection optical system 5 through an amplifier 6a to perform data processing thereto.

Figure 2:
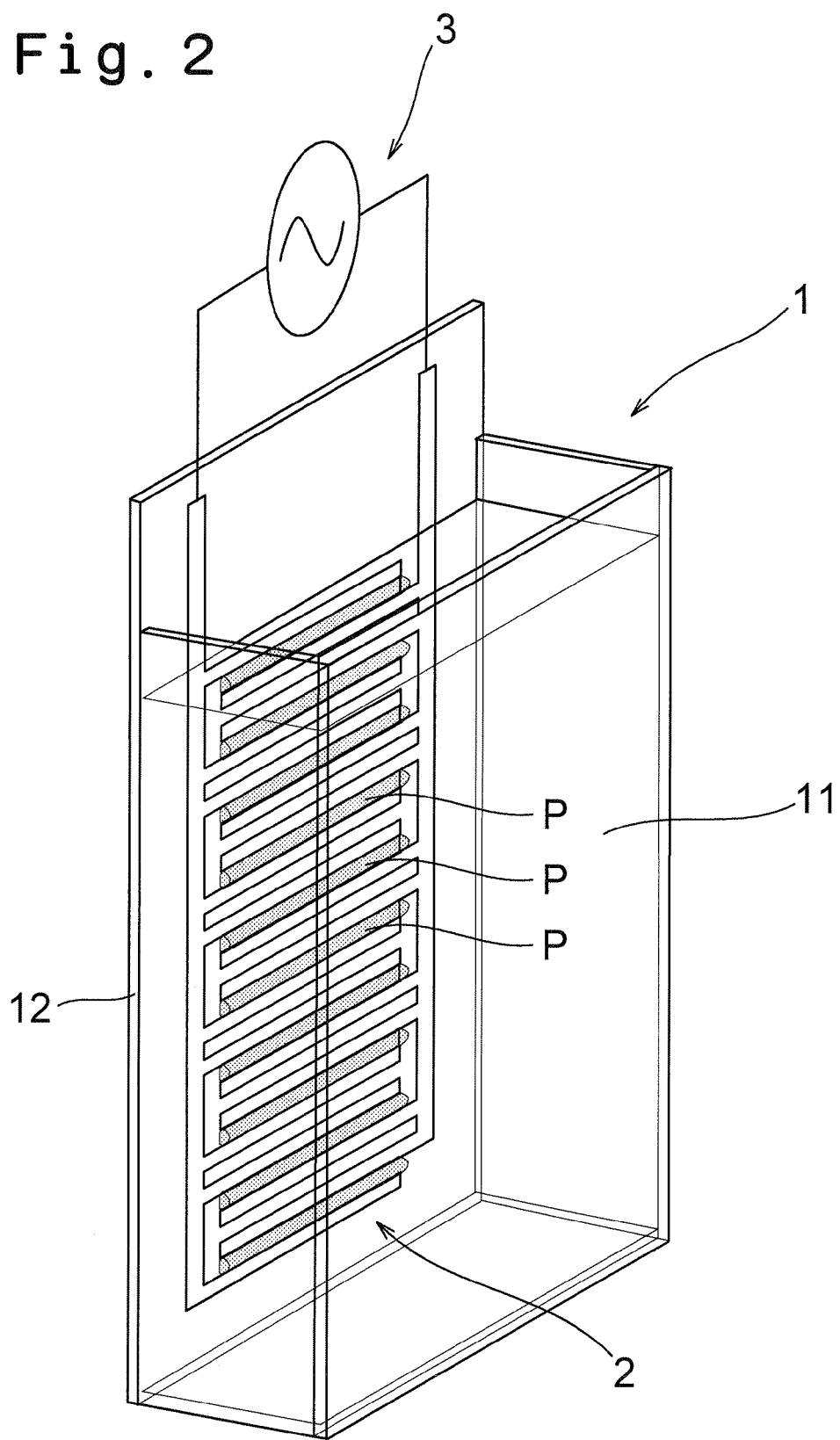
FIG. 2 is a perspective view of a concrete example of a cell 1 in FIG. 2, which includes a circuit diagram for applying voltage to an electrode pair 2.
Figure 3:
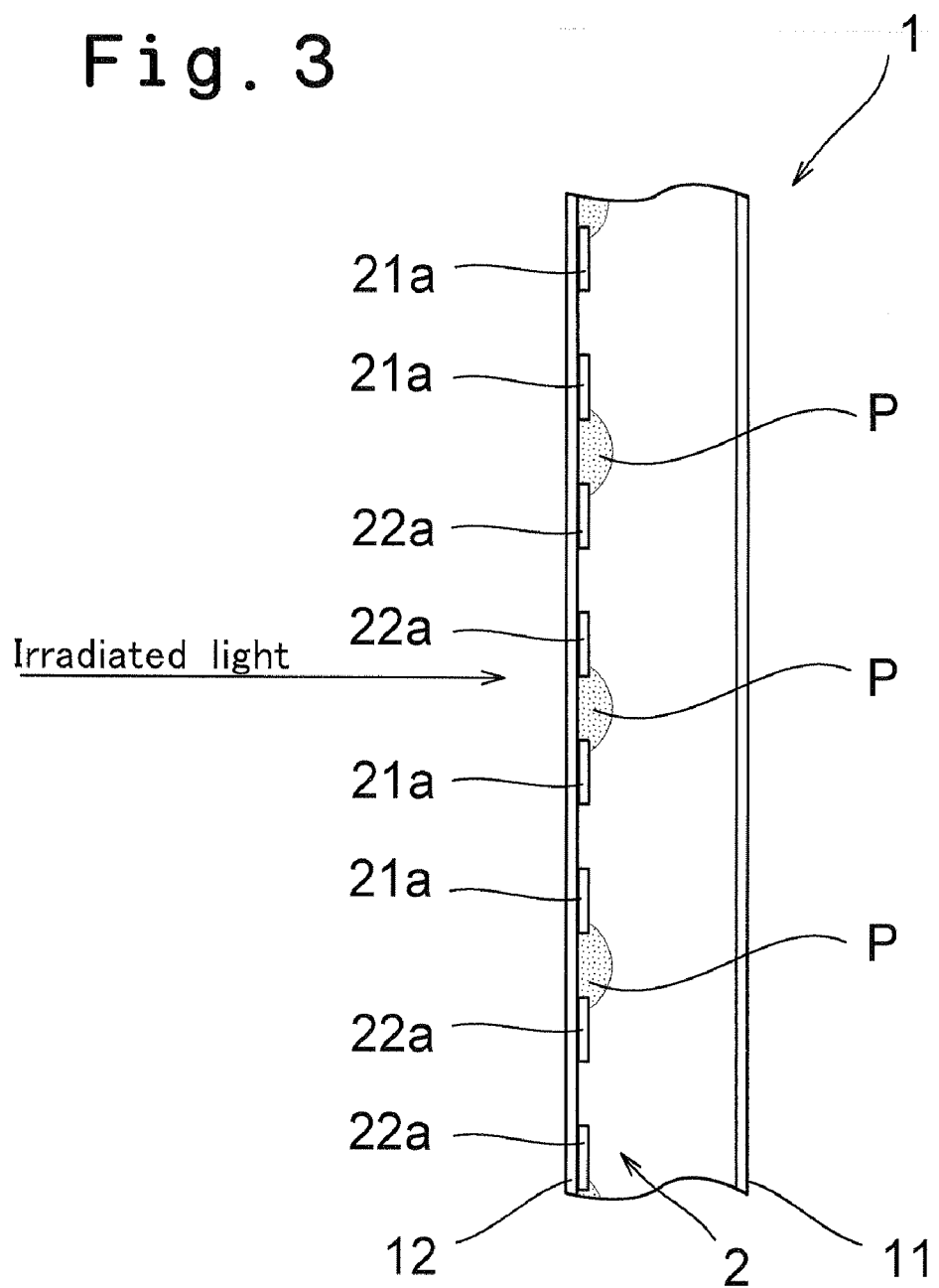
FIG. 3 is a schematic and partially enlarged sectional view of the cell in FIG. 1.

The cell 1 has at least mutually parallel wall bodies 11 and 12 each composed of a transparent material, as shown in the perspective view of FIG. 2 and the schematic enlarged sectional view of FIG. 3, and the electrode pair 2 is formed on a surface (inner surface) of one wall body 12.

Figure 4:
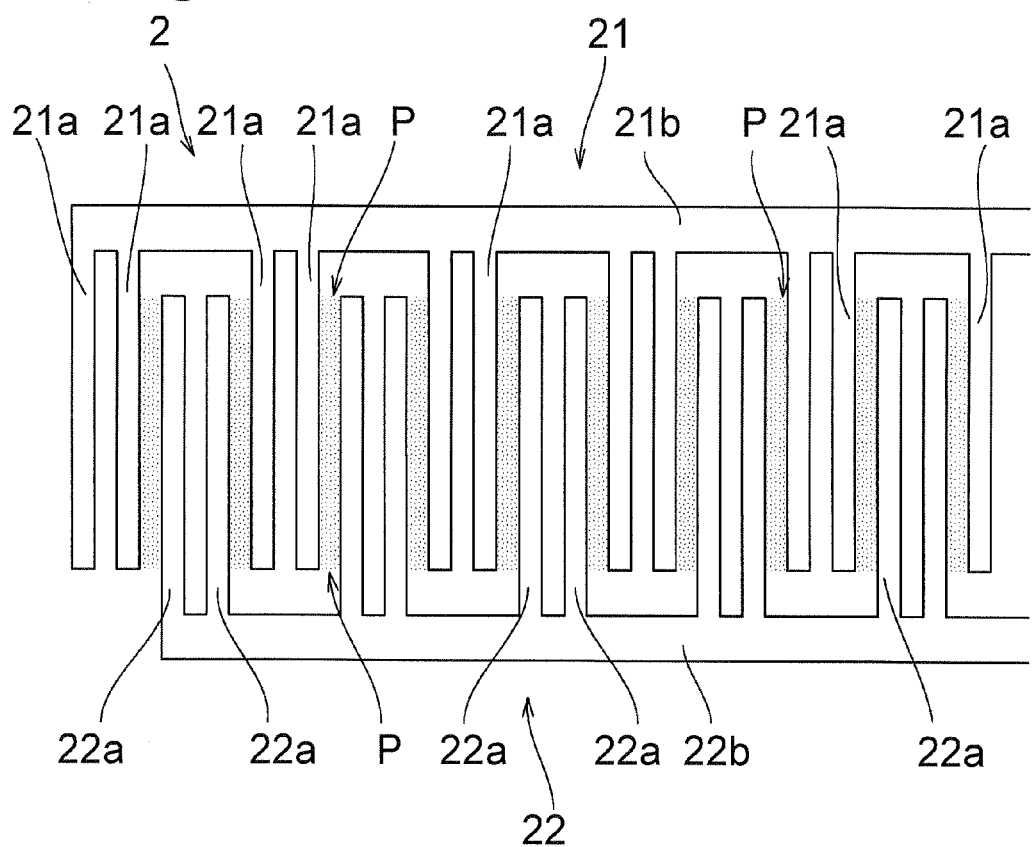
FIG. 4 is an illustrative view of an example of a pattern for the electrode pair 2 provided within the cell 1 in the embodiment of the present invention.

The electrode pair 2 is composed of electrodes 21 and 22, as shown in FIG. 4, which are comb-like electrodes each having a plurality of mutually parallel electrode pieces 21a or 22a and a connecting part 21b, 22b which electrically connects the respective electrode pieces 21a or 22a to each other. Each electrode 21, 22 has a shape in which an electrode piece eccentrically-located area having two linear electrode pieces 21a or 22a disposed adjacently to each other, and an electrode piece absent area free from electrode pieces are alternately formed. Namely, two of the electrode pieces 21a, 22a of each electrode 21, 22 are alternately located in parallel at regular intervals as the whole, with two electrode pieces 21a or 22a in the electrode piece eccentrically-located area of one electrode being fitted to the electrode piece absent area of the other.

When an AC (high frequency) voltage is applied from the electrode power source 3 to the electrode pair 2, an electric field distribution is generated in the sample stored in the cell 1 by this application of voltage, and the particles in the sample are migrated due to the field distribution as described later, whereby the diffraction grating by density distribution of the particles is generated. The output voltage of the electrode power source 3, and thus the applied voltage to the electrode pair 2 are controlled as described later by the device control and data retrieving processor 6.

The irradiation optical system 4 outputs a substantially monochromatic light while shaping it into a substantially parallel light flux, and the output light is irradiated toward the surface with the electrode pair 2 formed thereon of the cell 1. As the light source of the irradiation optical system 4, a one which emits only a monochromic light such as laser or LED is easy to use. However, a continuous wavelength light source can be used also if the light thereof is made pseudo-monochromic by a band pass filter, a spectrometer or the like, with a spectrum band width of about several tens nm or less, for example, in a visible wavelength band.

The detection optical system 5 is disposed, for example, in the outgoing direction of the first order light diffracted by the diffraction grating by density distribution of the particles within the cell 1 of the light from the irradiation optical system 4. The detection optical system 5 is composed of, for example, a pin hole 5a and a light detector 5b. The detection optical system 5 measures a change in diffracted light intensity by the diffraction grating by density distribution of particles in the cell 1 in time series. Since the diffraction spot of each order of the so-called Fraunhofer condition is formed at the focal point of a focusing lens when the parallel diffracted light outputted from the cell 1 at an angle of each order is converged by the focusing lens, the pin hole and the detector may be disposed in a necessary order position to detect the intensity therein.

In the above-mentioned configuration, when AC voltage is applied between the electrodes 21 and 22 constituting the electrode pair 2, the electric field distribution according to the electrode pattern is formed in the sample within the cell 1, and a density distribution of the particles is caused by dielectrophoresis based on the field distribution. Namely, in the electrode pair 2 of FIG. 4, a high density area P of particles is formed in a part where the electrode pieces of reverse polarities are mutually adjacent, or in a part where the electrode piece 21a of one electrode 21 is adjacent to the electrode piece 22b of the other electrode 22 as shown in FIG. 4. The high density area P of the particles is spatially repeatedly formed at twice the arrangement pitch of the electrode piece 21a or 22a in parallel to the electrode pieces 21a and 22a, and the diffraction grating is formed by a plurality of high density areas P of the particles.

The light from the irradiation optical system 4 is diffracted, when irradiated to such diffraction grating by density distribution of the particles, by the diffraction grating. The diffraction grating by density distribution of particles has grating pitch twice as large as that of the diffraction grating formed by the electrode pieces 21a and 22a, so the grating constants are different between both diffraction gratings, and diffracted light of a specific order determined by the grating constant of the diffraction grating formed by the density distribution of the particles appears in a direction where no diffracted light by the diffraction grating formed by the electrodes 21a and 22a is present.

Namely, in this embodiment, [2m+1]-order diffracted light (m is an integer) by the diffraction grating formed by the density distribution of particles is formed in directions where no diffracted light by the diffraction grating formed by the electrode pieces is present. Accordingly, by disposing the detection optical system 5 at one of these directions, background light independent from density diffraction grating can be kept low in the detection light by the detection optical system 5 to minimize fluctuation of background light or shot noise by background light. Consequently, the diffracted light from the diffraction grating by density distribution of the particles can be measured with satisfactory S/N. Therefore, by measuring the first order diffracted light for example, only the intended diffracted light from the diffraction grating by density distribution of the particles can be extracted while avoiding strong diffracted light from the electrode pieces. Since the light diffracted from each groove of the diffraction grating is interfered and added in the same phase as described above, the effect of increasing signals as the square of the number of grooves ensures measurements without being disturbed by the strong diffracted light from the electrode pieces 21a and 22a, and even weak dielectrophoresis can be consequently measured with satisfactory sensitivity.

It is known that the intensity of the electrophoresis phenomenon depends on the frequency of AC voltage applied, and the frequency dependency depends on complex dielectric constants that are electromagnetic properties of a particle and a dispersion medium of the particle. Therefore, this can be applied to analysis of properties of a particle and its dispersion medium.

Figure 5:
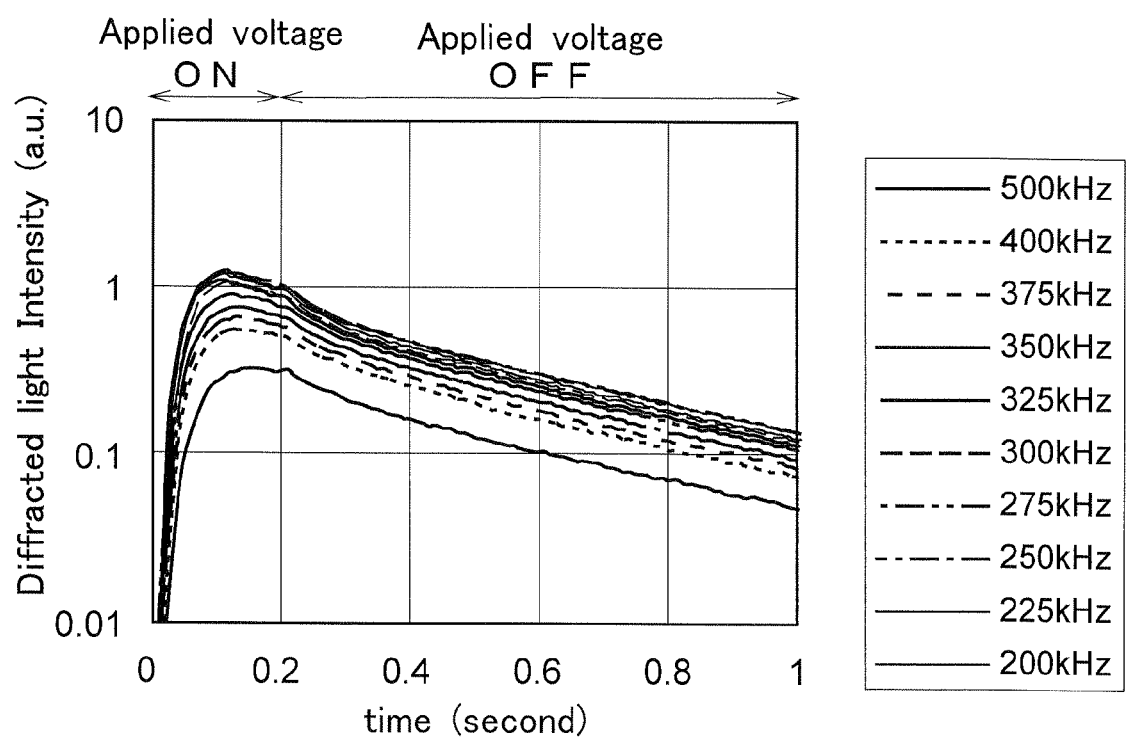
FIG. 5 is a graph showing an example of measuring result of diffracted light intensity, which is obtained by measuring the diffracted light intensity between generation of a diffraction grating by density distribution of particles and disappearance thereof by use of the apparatus of FIG. 1 by varying the frequency of AC voltage applied to the electrode pair 2.

FIG. 5 shows a measuring result of diffracted light intensity for a sample having silica particles of 8 nm in diameter dispersed in water as the medium, in which the diffracted light intensity is measured during the period between generation of the diffraction grating by density distribution of particles and disappearance thereof by use of the apparatus of FIG. 1 by varying the frequency of AC voltage applied to the electrode pair 2 to 10 kinds of frequency of 200 KHz to 500 KHz. In FIG. 5, the time up to 0.2 second is a time zone where the AC voltage is applied, or a time zone where dielectrophoresis is ON, during which the particles periodically collect to form the diffraction grating by density distribution. On and after 0.2 second, it is observed that the diffraction grating by density distribution of the particles once formed is exponentially relaxing due to diffusion phenomenon of particles after stopping the application of AC voltage.

The measurement by varying the frequency is extremely easy to carry out. According to actual measurements, the particles in the medium appear hardly changed even if application/stoppage of AC voltage is repeated, with the reproducibility being relatively retained. Therefore, data as shown in FIG. 5 can be easily collected by repeating the application/stoppage of voltage in a state where the sample including the particles dispersed in the medium is held in the cell 1 while successively varying the frequency.

Figure 6:
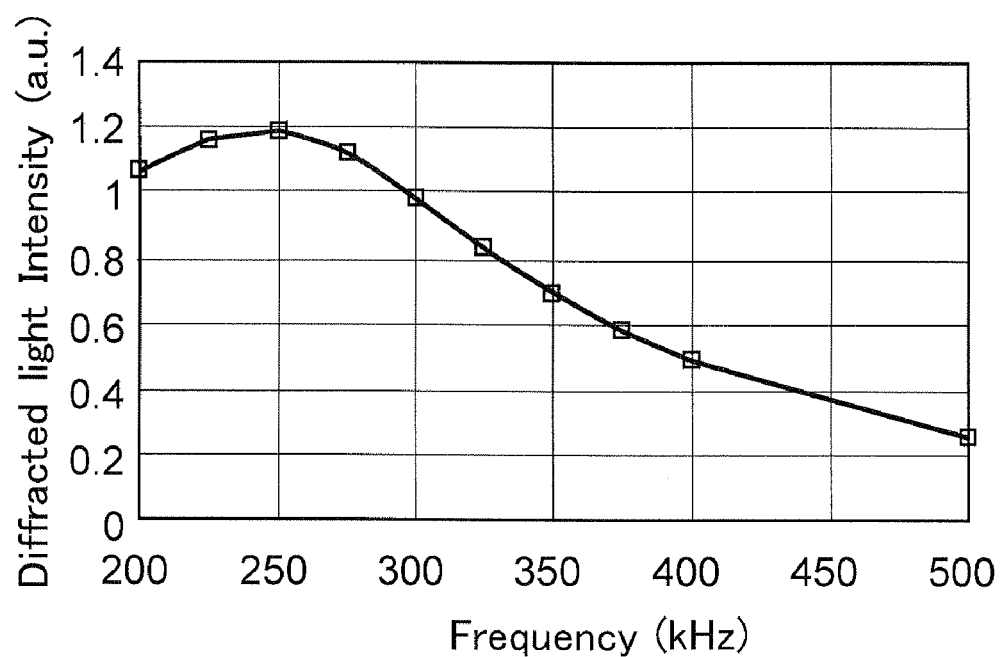
FIG. 6 is a graph showing the measuring result at the point of time 0.1 second in FIG. 5, which is plotted with the diffracted light intensity being on the vertical axis and the frequency on the horizontal axis.

The graph of FIG. 6 shows an indicative example of frequency dependency, in which the diffracted light intensity at the point of time 0.1 second in FIG. 5 is plotted with the diffracted light intensity being on the vertical axis and the frequency on the horizontal axis. It is generally known by an optical theory that the electric field formed by diffracted light is proportional to the modulation amplitude of a diffraction grating, and the intensity of the diffracted light is proportional to the square of the electric field. In other words, the square root of diffracted light intensity is proportional to the modulation amplitude of a diffraction grating. Therefore, the square root of the diffracted light intensity of the density grating generated in this embodiment is proportional to the modulation amplitude of the diffraction grating by particles density distribution formed by dielectrophoresis. FIG. 6 shows the relation of frequency to diffraction intensity, and if the vertical axis is converted to the square root, the modulation amplitude, which is one of indexes quantitatively showing the effect of dielectrophoresis can be obtained. In this way, information for complex dielectric constant that is a natural electro-optical characteristic of particle can be obtained from the frequency dependency of FIG. 6 as described later.

Figure 7:
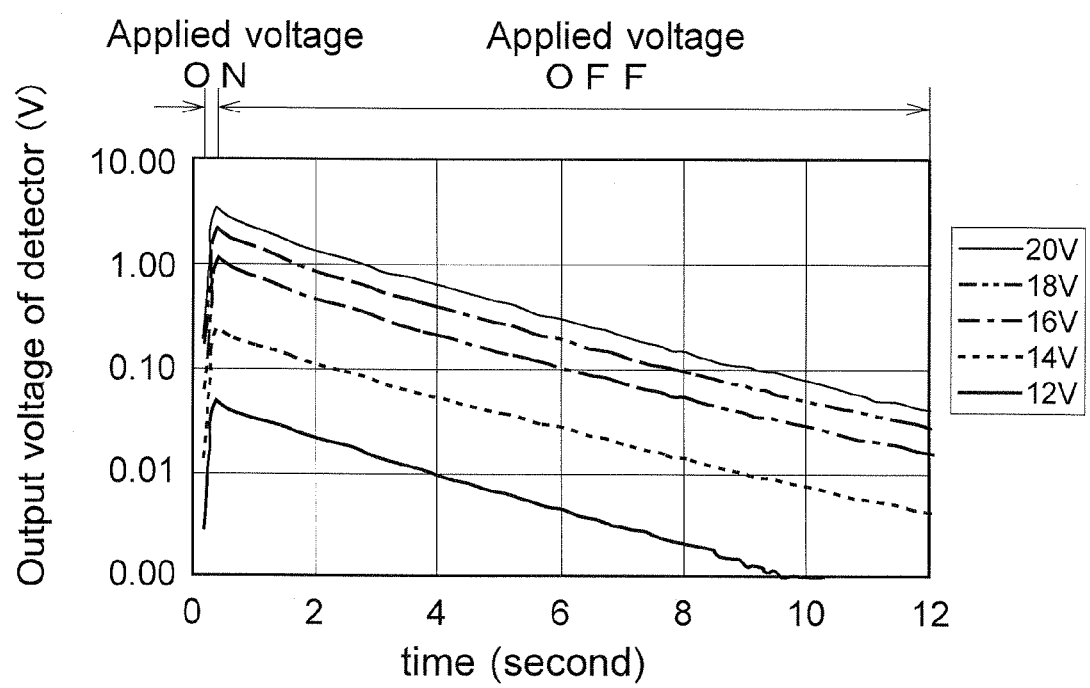
FIG. 7 is a graph showing a result of repeated measurements by using the apparatus in FIG. 1, with varying the amplitude of the AC voltage in formation of the diffraction grating by density distribution of particles while maintaining the frequency of the applied AC voltage constant.
Figure 8:
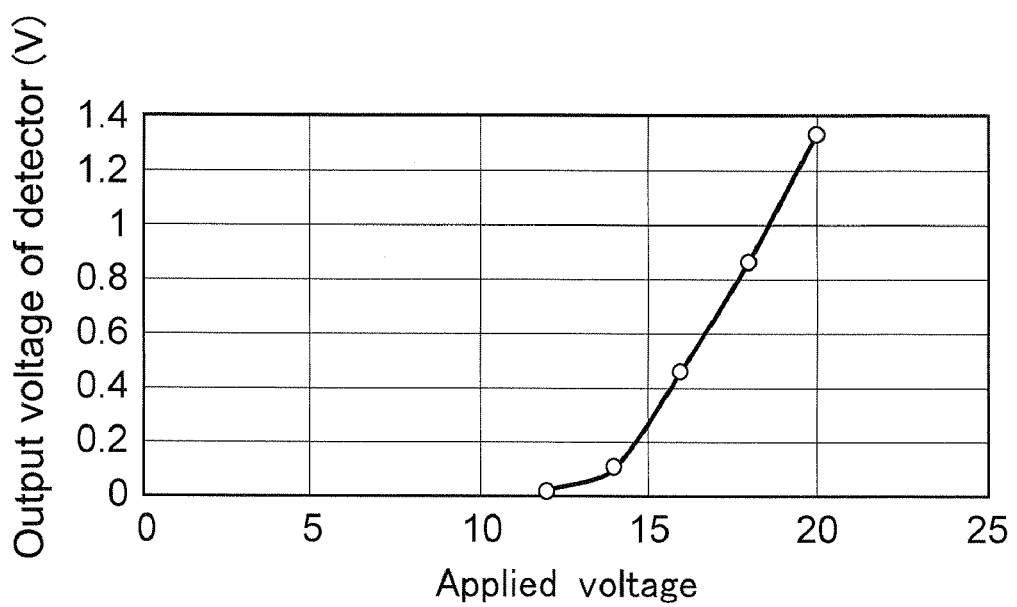
FIG. 8 is a graph in which the height of diffraction signal (detection voltage) at the point of time 2 seconds in FIG. 7 is plotted against the applied voltage.

The graph of FIG. 7 shows a result of repeated measurements, with varying the amplitude of the AC voltage applied in formation of the diffraction grating by density distribution of particles, from 12V to 20 V of peak-to-peak value on a 2-V-basis, while maintaining the frequency of the applied AC voltage constant (500 Hz). Although a larger absolute value of signal is shown at a higher voltage since the modulation of diffraction grating is of course larger as the voltage is higher, the exponential attenuation part on and after stopping the application of voltage is almost parallel. Namely, since the particles become dielectrophoretically free and simply return to an original equilibrated state by diffusion phenomenon when the application of voltage is stopped, the returning rate (attenuation coefficient) is determined depending on diffusion coefficient D. Therefore, the magnitude of diffraction signal at an appropriate point of time in FIG. 7 is plotted to the voltage in formation of the diffraction grating by particle density distribution, whereby FIG. 8 is obtained. As is apparent from FIG. 8, in which the height of signal (output voltage of detector) at the point of time 2 seconds in FIG. 7 is plotted, the diffraction signal has a characteristic such that it does not occur up to a certain threshold voltage and suddenly rises up at a voltage beyond the threshold. The threshold is related to the magnitude relation which describes if the dielectrophoretic potential $\phi_{dep}$ represented by the following equation (1) exceeds the thermal energy kT or not.

[Mathematical Expression 1]

$$\phi_{dep} = 2\pi a^3 e_m Re[K^*(\omega)] E^2 \quad (1)$$

wherein "a" is the radius of a particle, ω is the dielectric constant of a dispersion medium, ω is an angular frequency, which is 2π-fold the frequency "f" of AC used for grating formation, and E is electric field strength.

[Mathematical Expression 2]

$$Re[K^*(\omega)]$$

is a real part of the so-called Clausius-Mosotti coefficient K*(ω), and K*(ω) is a quantity given by the following equation (2).

[Mathematical Expression 3]

$$K^*(\omega) = \frac{\varepsilon_p^* - \varepsilon_m^*}{\varepsilon_p^* + 2\varepsilon_m^*} \quad (2)$$

wherein $\varepsilon_p^*$ and $\varepsilon_m^*$ represent complex dielectric constants of the particle and the medium, which are given respectively by:

[Mathematical Expression 4]

$$\varepsilon_p^* = \varepsilon_p - j\frac{\sigma_p}{\omega}$$
$$\varepsilon_m^* = \varepsilon_m - j\frac{\sigma_m}{\omega} \quad (3)$$

In the equation (2), the mark * shows that each dielectric constant is a complex number, and in the equation (3), $\varepsilon_p$ and $\varepsilon_m$ represents dielectric constants of the particle and the medium, respectively, $\sigma_p$ and $\sigma_m$ represent conductivities of the particle and the medium, respectively, "j" represents the imaginary unit, and ω represents an angular frequency of high frequency applied.

The dependency on frequency "f" shown in FIG. 6 relates to K*(ω) shown in the equation (1). The angular frequency, which is ω=2πf, is found to be connected to K*(ω) through ω contained in $\varepsilon_p^*$ and $\varepsilon_m^*$ of the equation. Namely, the form of K*(ω) can be predicted from the dependency on frequency "f".

The estimation of FIG. 8 also involves the equation (1). Since dielectrophoresis is observed only when the dielectrophoretic potential $\phi_{dep}$ of the equation (1) exceeds the thermal energy kT, the diffraction grating by particle density distribution is induced thereby. The existence of a threshold of dielectrophoresis is thus explained. From FIG. 8 that shows the threshold and signal rise-up manner, the complex dielectric constants of the particle and the dispersion medium can be explained using the equation (1) relating with the above-mentioned frequency characteristics of FIG. 6.

A number of traces as shown in FIGS. 5 and 7 can be automatically obtained for one sample in a short time by use of the apparatus shown in FIG. 1 while successively varying the frequency and the applied voltage. Accordingly, further information related to properties of a nanoparticle and a dispersion medium thereof can be acquired by converting and displaying such traces in a diagram of frequency (such as FIG. 6) or in a diagram of applied voltage (field intensity, such as FIG. 8).

The K*(ω) shown in the equation (2) is generally a complex number, and its real part becomes positive or negative depending on the complex dielectric constants $\varepsilon_p^*$ and $\varepsilon_m^*$ of particle and medium. The positive and negative of this quantity corresponds to a positive migrating force for capturing particles by attraction and a negative migrating force which appears as repulsive force, and in both cases, the technique of density diffraction grating can be applied.

Although the signal in the generation process of the density distribution of the particles is used in the above description, the relaxation rate of the diffraction grating after stopping the application of AC voltage to the electrode pair 2 can be also used.

Namely, when the application of AC voltage to the electrode pair 2 is stopped after generating the diffraction grating by density distribution of the particles by the application of AC voltage, the particles start to diffuse, and the diffraction grating eventually disappears. The exponential attenuation of diffracted light intensity by the relaxation of grating can be represented by the following equation with the intensity before attenuation being $I_0$ and the intensity at time "t" being "I".

[Mathematical Expression 5]

$$I = I_0 \exp\left[-2\left(\frac{2\pi}{\Lambda}\right)^2 Dt\right] \quad (4)$$

wherein Λ represents the pitch of grooves of the diffraction grating by density distribution, and "D" is the diffusion coefficient of particles.

In FIG. 5, the diffusion coefficient "D" can be determined from the attenuation coefficient of signal intensity $2(2\pi/\Lambda)^2 D$ on and after time 0.2 second at which the voltage application is stopped to stop dielectrophoresis, and the particle radius "a" can be determined from "D" using the following relation known as the Einstein-Stokes equation.

[Mathematical Expression 6]

$$D = \frac{kT}{6\pi\eta a} \quad (5)$$

In the formula (5), "k" represents Boltzmann's constant, "T" represents absolute temperature, and η is the viscosity coefficient of a medium. The equation (1), which shows the dependency of dielectrophoresis force potential $\phi_{dep}$ on the field intensity E, contains the cube of the particle radius "a". When the particle radius "a" is obtained, information on other factors than the particle radius in the equation (1) can be extracted by correcting the effect of the cube of "a".

It can be summarized that the above-mentioned measurement method which utilizes the combination of generation and attenuation of diffraction grating is characterized by that the method enables us to perform extremely efficient evaluation and is particularly useful for a nanoparticle with unknown particle size, because two kinds of information can be obtained at once by acquiring a particle size from the latter attenuation term of FIG. 5, and determining characteristics of dielectrophoresis from the frequency dependency or field intensity dependency in the generation process of the grating.

INDUSTRIAL AVAILABILITY

According to the present invention, evaluation of dielectrophoresis can be simplified because the procedure is just to measure diffracted light without adhering a phosphor to a particle, and the quantitative determination property of measurement can be enhanced. Further, the sensitivity which was the most serious problem in measurement of dielectrophoresis can be so improved that the new method opens the way to obtaining dielectrophoretic characteristics of microparticles several nm in diameter which generally exhibit very weak dielectrophoretic effect.

Since determination of particle size can be performed using the same device from information in the disappearing process of diffraction grating by density distribution of particles, the intensity of dielectrophoresis can be analyzed, including correction with the particle size.

It is extremely useful for evaluation of protein particles or polymers in biotechnology, or in powder field and the like, because dielectrophoretic force of particles can be quantitatively evaluated, and the method and apparatus of the present invention are expectable as important measurement tools for various studies and developments in these fields.

The invention claimed is:

1. A dielectrophoretic intensity evaluation method, comprising the steps of:
    forming a distribution of AC electric field regularly arranged in a cell while storing a sample having particles dispersed in a medium in the cell, thereby dielectrically migrating the particles in the medium to generate a diffraction grating by density distribution of the particles;
    detecting diffracted light generated by irradiating the diffraction grating by density distribution with measuring light; and
    evaluating characteristics for dielectrophoretic intensity of the particles and/or the medium from the detection result.

2. The dielectrophoretic intensity evaluation method according to claim 1, wherein the operation of forming the distribution of AC electric field in the cell while storing the sample having the particles dispersed in the medium in the cell, thereby dielectrically migrating the particles in the medium to generate the diffraction grating by the particles, and detecting the diffracted light generated by irradiating the diffraction grating with measuring light is performed to the same sample more than once by varying frequency of the AC electric field, and frequency dependency of the dielectrophoretic intensity or dielectrophoretic sensitivity of the sample is evaluated based on a difference in detection result of each diffracted light.

3. The dielectrophoretic intensity evaluation method according to claim 1, wherein the operation of forming the distribution of AC electric field in the cell while storing the sample having the particles dispersed in the medium in the cell, thereby dielectrically migrating the particles in the medium to generate the diffraction grating by the particles, and detecting the diffracted light generated by irradiating the diffraction grating with measuring light is performed to the same sample more than once by varying intensity of the AC electric field, and field intensity dependency of the dielectrophoretic intensity or dielectrophoretic sensitivity of the sample is evaluated based on a difference in detection result of each diffracted light.

4. A dielectrophoretic intensity evaluation method, comprising:
    forming a distribution of AC electric field regularly arranged in a cell while storing a sample having particles dispersed in a medium in the cell, thereby dielectrically migrating the particles in the medium to generate a diffraction grating by density distribution of the particles; and
    performing evaluation for dielectrophoretic intensities of the particles and/or the medium, using diffracted light intensity information obtained by detecting diffracted light generated by irradiating the diffraction grating by density distribution with measuring light, and further particle size information obtained from a temporal attenuation rate of the diffracted light after interrupting the AC electric field.

5. An apparatus for evaluating dielectrophoretic intensity, comprising:
    a cell for holding a sample having particles dispersed in a medium;
    an AC power source;
    a pair of electrodes for forming an electric field distribution regularly arranged in the cell by application of voltage from the AC power source;
    a light source for irradiating a diffraction grating resulting from a density distribution caused by dielectrophoresis of the particles by formation of the electric field with measuring light;
    a light detector for detecting diffracted light of the measuring light by the diffraction grating; and
    a recording means for recording output of the light detector, in which magnitude of diffracted light intensity based on a time when the application of voltage to the electrodes is not performed is used as a dielectrophoretic evaluation signal.

6. The apparatus for evaluating dielectrophoretic intensity according to claim 5, wherein in addition to use of the magnitude of diffracted light intensity based on a time when the application of voltage to the electrodes is not performed as the dielectrophoretic evaluation signal, and a temporal attenuation rate of the diffracted light after interrupting the AC power source is measured to obtain particle size information of the particles.

* * * * *